United States Patent
Gibertoni

(10) Patent No.: US 7,686,015 B2
(45) Date of Patent: *Mar. 30, 2010

(54) DISPOSABLE ACTIVE HUMIDIFIER FOR THE MECHANICAL VENTILATION OF A PATIENT

(75) Inventor: Lucio Gibertoni, Mirandola (IT)

(73) Assignee: Mallinckrodt Inc., St. Louis, MS (US)

( * ) Notice: Subject to any disclaimer, the term of this patent is extended or adjusted under 35 U.S.C. 154(b) by 852 days.

This patent is subject to a terminal disclaimer.

(21) Appl. No.: 11/066,799

(22) Filed: Feb. 25, 2005

(65) Prior Publication Data

US 2005/0166915 A1 Aug. 4, 2005

Related U.S. Application Data

(63) Continuation of application No. 10/364,227, filed on Feb. 11, 2003, now Pat. No. 6,904,911, which is a continuation of application No. 10/331,362, filed on Dec. 30, 2002, now abandoned, which is a continuation of application No. 09/673,594, filed as application No. PCT/US99/08699 on Apr. 21, 1999, now Pat. No. 6,510,848.

(30) Foreign Application Priority Data

Apr. 22, 1998 (IT) .............................. MI98A0862

(51) Int. Cl.
*A62B 18/08* (2006.01)
(52) U.S. Cl. ........................ 128/201.13; 128/203.16; 128/203.17; 261/101; 261/104
(58) Field of Classification Search ............ 128/201.13, 128/203.16, 203.17; 261/101, 104
See application file for complete search history.

(56) References Cited

U.S. PATENT DOCUMENTS

| 3,228,876 | A | 1/1966 | Mahon |
| 3,927,981 | A | 12/1975 | Vinnay et al. |
| 4,031,012 | A | 6/1977 | Gics |
| 4,086,305 | A | 4/1978 | Dobritz |
| 4,098,852 | A | 7/1978 | Christen et al. |
| 4,146,597 | A | 3/1979 | Eckstein et al. |
| 4,155,961 | A | 5/1979 | Benthin |
| 4,381,267 | A | 4/1983 | Jackson |

(Continued)

FOREIGN PATENT DOCUMENTS

JP 5319879 6/1978

(Continued)

OTHER PUBLICATIONS

Japanese Office Action with Translation, Patent Application No. 2000-544385, 4 pages, Jun. 19, 2007.

(Continued)

*Primary Examiner*—Darwin P Erezo

(57) ABSTRACT

A disposable active humidifier for the mechanical ventilation of a patient, which has the particularity that it comprises a cartridge which forms a humidification chamber which is delimited by an inlet and by an outlet and can be interposed in the ventilation circuit. The cartridge has an interspace which is externally delimited by a heat exchange surface and is internally delimited by a hydrophobic membrane which surrounds the humidification chamber. A humidification fluid, originating from a bottle or bag, can be introduced in the interspace.

10 Claims, 2 Drawing Sheets

U.S. PATENT DOCUMENTS

| | | | |
|---|---|---|---|
| 4,449,992 A | 5/1984 | Yamada et al. | |
| 4,859,331 A | 8/1989 | Sachtler et al. | |
| 4,910,384 A | 3/1990 | Silver | |
| 5,062,145 A | 10/1991 | Zwaan et al. | 392/396 |
| 5,192,499 A | 3/1993 | Sakai et al. | |
| 5,195,515 A * | 3/1993 | Levine | 128/203.26 |
| 6,510,848 B1 | 1/2003 | Gibertoni | |

FOREIGN PATENT DOCUMENTS

| | | |
|---|---|---|
| JP | 6253193 | 11/1987 |
| JP | 09280783 | 10/1997 |
| WO | 96/20747 | 7/1996 |

OTHER PUBLICATIONS

EP Search report for EP Patent Application No. 99919933 - 3 pages.

* cited by examiner

DISPOSABLE ACTIVE HUMIDIFIER FOR THE MECHANICAL VENTILATION OF A PATIENT

This is a continuation of Ser. No. 10/364,227 filed Feb. 11, 2003, now U.S. Pat. No. 6,904,911 which is a continuation of Ser. No. 10/331,362 filed Dec. 30, 2002, abandoned, which is a continuation of Ser. No. 09/673,594 filed Oct. 18, 2000, now U.S. Pat. No. 6,510,848, which is the U.S. national phase of PCT international application No. PCT/US99/08699 filed Apr. 21, 1999, which claims priority from Italian Application No. MI98 A 000862 filed Apr. 22, 1998.

The present invention relates to a disposable active humidifier for the mechanical ventilation of a patient.

It is known that the mechanical ventilation of a patient uses dry gases which are humidified before being inspired by the patient. Most commercially available systems are based on the principle of making the gas flow directly over the water contained in a heated container.

The conventional solution has a drawback which is constituted by the relatively high volume of the cartridge, which constitutes an additional bulk; it should be noted that it is very important to reduce bulk, since in mechanical ventilation, in which the pressure of the ventilator expands the lungs of the patient to ventilate him, an extra compressible space is certainly a negative factor.

The aim of the invention is indeed to eliminate the drawbacks mentioned above, which are typical of conventional systems (bacterial contamination and high compressible volume), by providing a disposable active humidifier for the mechanical ventilation of a patient which has a very small bulk and in particular constitutes an integrated segment in the ventilation circuit and in practice therefore does not increase the volume of compressible air.

Within the scope of this aim, a particular object of the invention is to provide a disposable active humidifier which can be prepared in a sterile package which can be connected only once to the patient without requiring further handling with the risk of bacterial contamination.

Another object of the present invention is to provide an active humidifier in which the water remains confined within the cartridge with a continuous supply which in practice forms a closed circuit with no need for connection to the outside.

Another object of the present invention is to provide a disposable active humidifier which, by virtue of its particular constructive characteristics, is capable of giving the greatest assurances of reliability and safety in use.

This aim, these objects and others which will become apparent hereinafter are achieved by a disposable active humidifier for the mechanical ventilation of a patient, according to the invention, characterized in that it comprises a cartridge which forms a humidification chamber which is delimited by an inlet and by an outlet and can be interposed in a ventilation circuit, said cartridge having an interspace which is externally delimited by a heat exchange surface and is internally delimited by a hydrophobic membrane which surrounds said humidification chamber, a humidification fluid being introducible in said interspace.

Further characteristics and advantages will become apparent from the description of a preferred but not exclusive embodiment, illustrated only by way of non-limitative example with the aid of the accompanying drawings, wherein.

Figure 1:
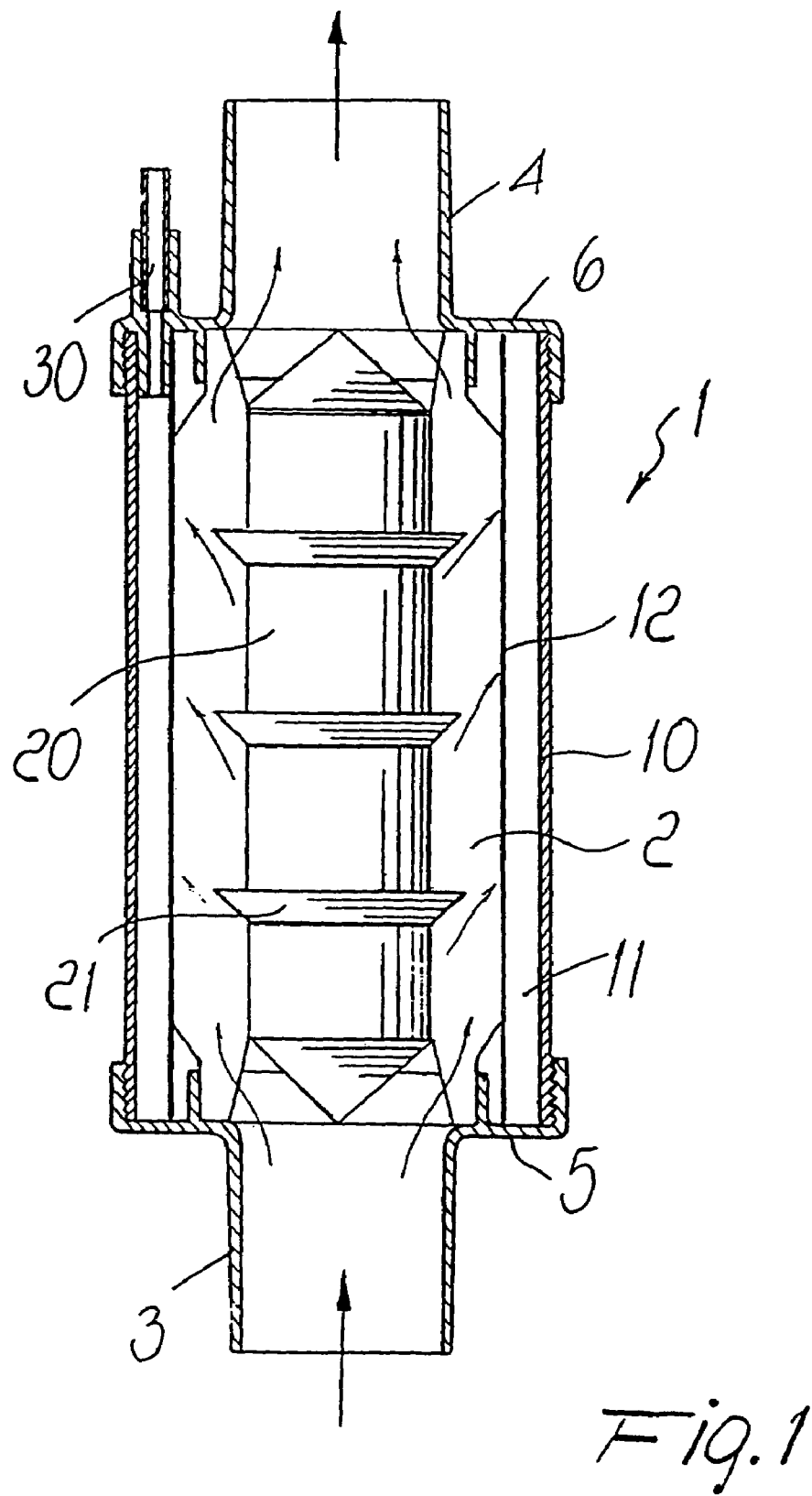
FIG. 1 is a schematic sectional view of a disposable active humidifier according to the invention.

With reference to the above figures, the disposable active humidifier for the mechanical ventilation of a patient comprises a cartridge, generally designated by the reference numeral 1, which internally forms a humidification chamber 2 which is delimited by an inlet 3 and by an outlet 4 which are formed on respective caps 5 and 6 which are arranged mutually opposite at the axial ends of the humidification chamber 2.

The cartridge 1 is externally provided with a heat exchange surface, advantageously constituted by a tubular aluminum casing 10, which delimits an interspace 11 formed by a hydrophobic membrane 12 which delimits the humidification chamber 2.

Inside the humidification chamber 2 there is a diffuser 20 which is meant to direct the incoming air stream so that it flows over the membrane 12, so as to facilitate the transfer of humidity through the hydrophobic membrane 12 that delimits the interspace 11, inside which water is introduced by means of an inlet 30, to which it is possible to connect a simple bag or bottle which continuously introduces the water into the interspace so that by means of the hydrophobic membrane it is possible to ensure the required degree of humidity of the air.

It should be added that the diffuser advantageously has protrusions 21 shaped like a conical inclined surface, spaced apart from the membrane, which facilitate the conveyance of the air stream against the membrane, which provides a barrier against bacteria, so that the system can be supplied with ordinary distilled water, thus reducing the operating costs.

The cartridge 1 can be easily used in a ventilation circuit, designated schematically by the reference numeral 40 in the drawing, in which there is a heater 41 which forms the seat for accommodating the external casing of the cartridge.

From the above description it is thus evident that the invention achieves the intended aim and objects, and in particular the fact is stressed that the particular structure that has been used allows to provide a disposable active humidifier which in practice does not increase the volume of air present in the ventilation circuit, since it provides a simple segment which is interposed in the ventilation circuit itself.

Furthermore, the new active humidifier is based on an innovative principle which is different from the other systems that are commercially available, since its humidification principle is based on the vaporization of water instead of on flowing over water present in a heated container.

The present system uses a humidifier cartridge which is integrated in the temperature-controlled ventilation circuit and which by vaporization charges the dry gases on the inspiratory line of the patient with humidity.

By virtue of the PVC temperature-controlled circuit in which the heating resistor is embedded in the external reinforcement spiral, the humidity released by the humidifier cartridge does not condense along the inspiratory line but is transferred in full to the patient.

The cartridge of the humidifier (see FIG. 1) is constituted by an external body made of metal (aluminum) which acts as interface with the heating element of the humidifier. Inside the cartridge there is a hydrophobic membrane which provides the interface between the liquid and the vapor phase of the inspiratory line.

The hydrophobic membrane allows the passage of the vapor that forms as a consequence of the heating of the water contained in the cartridge.

The system can be supplied with ordinary sterile/double-distilled water.

Figure 2:
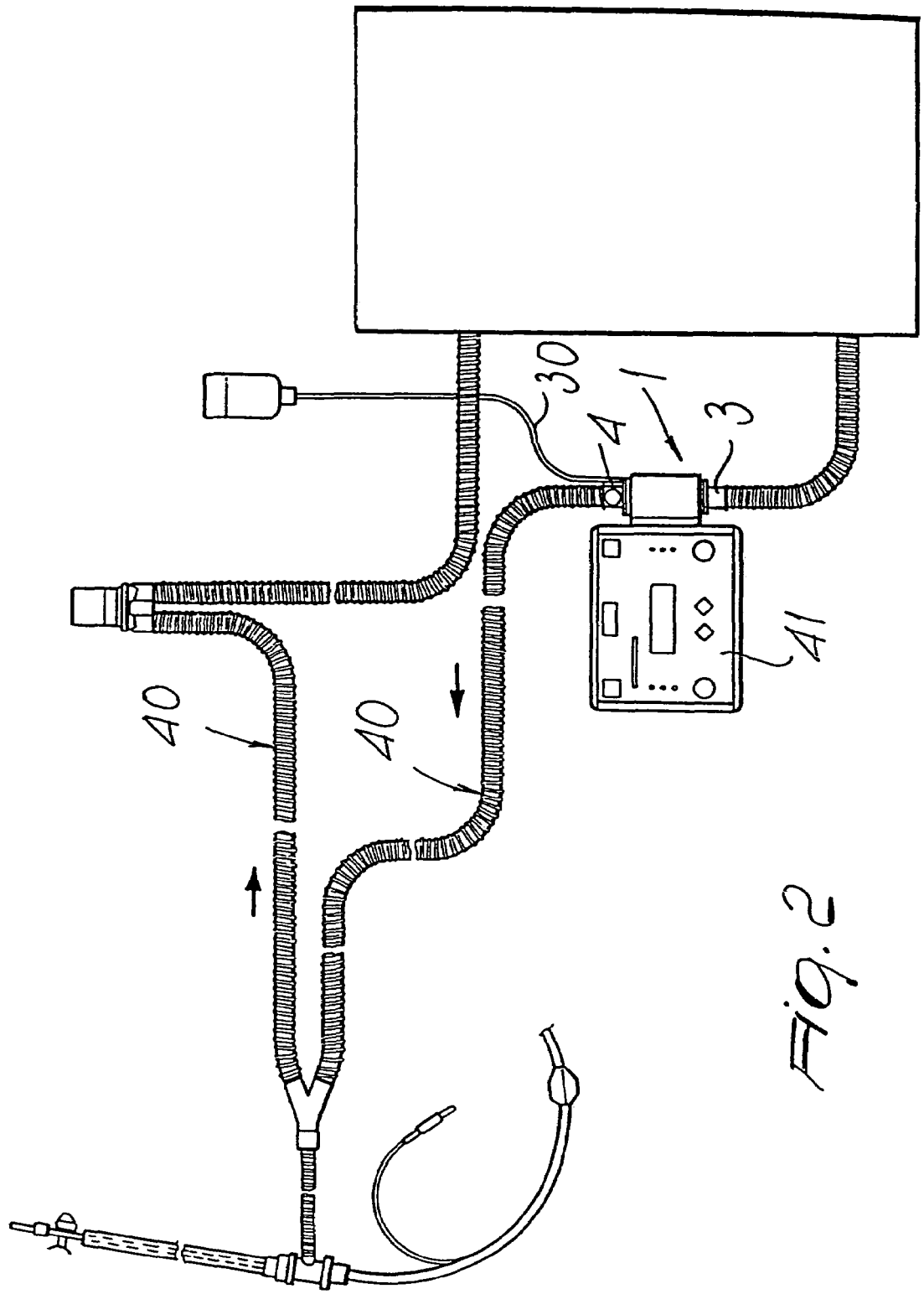
FIG. 2 is a schematic view of the active humidifier included in a ventilation circuit.

The innovation of the system is that it uses a cartridge which is integrated in the circuit (see the drawing in the accompanying FIG. 2) and is preassembled to the ventilator with the connections provided.

Differently from flow-over humidification systems, the present system eliminates the contact of the supply water with the outside environment, avoiding the risk of exogenous contamination of the patient and keeping the system dry without forming condensate in the ventilation circuit.

The invention thus conceived is susceptible of numerous modifications and variations, all of which are within the scope of the inventive concept.

All the details may furthermore be replaced with other technically equivalent elements.

In practice, the materials used, as well as the contingent shapes and the dimensions, may be any according to the requirements.

The invention claimed is:

1. A system for humidifying breathing gas in a ventilation circuit for mechanical ventilation of a patient, comprising:
   a ventilation circuit for providing a dry breathing gas for mechanical ventilation of a patient;
   a humidifier cartridge interposed in said ventilation circuit for humidifying said dry breathing gas in said ventilation circuit, said humidifier cartridge including:
      an inlet and an outlet connected to said ventilation circuit,
      a humidification chamber disposed between said inlet and said outlet, and
      a hydrophobic membrane disposed in said humidification chamber, said hydrophobic membrane disposed within an external heat exchange surface at least partially defining an interspace between said hydrophobic membrane and said external heat exchange surface;
      a stationary diffuser disposed inside said humidification chamber, said diffuser including multiple distinct protrusions spaced apart from said hydrophobic membrane such that said diffuser protrusions divert the breathing gas toward said hydrophobic membrane and along a pathway defined between the outer edges of said diffuser protrusions and said hydrophobic membrane;
   a heater disposed in relationship with said external heat exchange surface for transferring heat across said external heat exchange surface to a volume of humidification fluid located in said interspace in order to heat said humidification fluid; and
   a supply of humidification fluid connected to said interspace for introducing said humidification fluid into said interspace, said hydrophobic membrane being operable to transfer humidity through the hydrophobic membrane from said humidification fluid into said humidification chamber.

2. The system of claim 1, wherein said heater is operative to vaporize said humidification fluid to charge the dry breathing gas with humidity through said hydrophobic membrane.

3. The system of claim 1, wherein said interspace includes a fluid inlet for receiving said humidification fluid, said humidification fluid comprises water, and said supply of humidification fluid comprises means for providing said interspace with a continuous supply of water through said fluid inlet.

4. The system of claim 1, wherein said humidifier cartridge is at least partially housed within said heater.

5. The system of claim 1, wherein said humidification fluid is physically separated from said heater at least by said external heat exchange surface.

6. The system of claim 1, wherein said humidifier cartridge and said heater are configured for heating said humidification fluid through said external heat exchange surface after said humidification fluid is introduced into said interspace from said supply of humidification fluid.

7. A humidifier cartridge configured to be interposed in a breathing circuit for providing breathing gas to a patient, comprising:
   an inlet and an outlet connected to said breathing circuit;
   a humidification chamber disposed between said inlet and said outlet;
   a hydrophobic membrane disposed in said humidification chamber;
   an interspace within said humidification chamber configured to house a volume of humidification fluid, said interspace at least partially defined by said hydrophobic membrane;
   a stationary diffuser disposed inside said humidification chamber, said diffuser including multiple distinct protrusions spaced apart from said hydrophobic membrane such that said diffuser protrusions divert the breathing gas toward said hydrophobic membrane and along a pathway defined between the outer edges of said diffuser protrusions and said hydrophobic membrane; and
   a heat exchange surface of said humidification chamber, said heat exchange surface providing an interface for transferring heat from a heater external to said humidification chamber to humidification fluid in said interspace in order to heat said humidification fluid.

8. The humidifier cartridge of claim 7, wherein said heat exchange surface comprises an external surface of said humidification chamber.

9. The humidifier cartridge of claim 7, wherein said heat exchange surface is configured to physically separate said heater from humidification fluid in said interspace.

10. The humidifier cartridge of claim 7, wherein said humidifier cartridge is configured to be at least partially housed within said external heater.

\* \* \* \* \*